United States Patent [19]

Puppel

[11] Patent Number: 5,055,630
[45] Date of Patent: Oct. 8, 1991

[54] PROCESS FOR MAKING P-XYLENE WITH A PURITY OF MORE THAN 99.8% BY WEIGHT

[75] Inventor: Günter Puppel, Wulfen, Fed. Rep. of Germany

[73] Assignee: Krupp Koppers GmbH, Essen, Fed. Rep. of Germany

[21] Appl. No.: 425,044

[22] Filed: Oct. 20, 1989

[30] Foreign Application Priority Data

Nov. 19, 1988 [DE] Fed. Rep. of Germany ....... 3839229

[51] Int. Cl.⁵ .............................................. C07C 7/14
[52] U.S. Cl. .................................... 585/814; 885/812; 885/816; 885/817
[58] Field of Search ................. 585/812, 814, 816, 817

[56] References Cited

U.S. PATENT DOCUMENTS

| | | | |
|---|---|---|---|
| 2,398,526 | 4/1946 | Greenburg | 585/812 X |
| 2,614,134 | 10/1952 | Powers | 585/812 |
| 2,827,503 | 3/1958 | Kennel et al. | 585/812 |
| 2,885,431 | 5/1959 | Tarr | 585/812 X |
| 2,890,239 | 6/1959 | Quigg | 585/812 X |
| 3,462,508 | 8/1969 | Dresser et al. | 585/812 X |
| 3,541,804 | 11/1970 | Wiegandt et al. | 585/817 X |
| 3,643,453 | 2/1972 | Groothuis et al. | 585/817 X |
| 3,720,647 | 3/1973 | Gelbe et al. | 585/816 |
| 3,798,282 | 3/1974 | Bemis et al. | 585/812 X |

FOREIGN PATENT DOCUMENTS 1024100 3/1966 United Kingdom ................. 585/814

Primary Examiner—Curtis R. Davis
Assistant Examiner—William C. Diemler
Attorney, Agent, or Firm—Michael J. Striker

[57] ABSTRACT

The process for obtaining a p-xylene final product more than 98% pure from a crystalline starting material with a purity of about 98%, includes the steps of intermixing the starting material with precooled water and fed back recovered p-xylene in a mixer at a temperature of 0° to 13° C. to form a p-xylene-crystal-water mixture containing p-xylene crystals and water; continuously transferring the mixture produced as soon as it contains about 30% by weight p-xylene crystals into a purifying centrifuge via a dewatering filter to form a fluid phase and a p-xylene crystal slurry; separating the fluid phase further from the p-xylene crystals in a first stage of a purifying centrifuge, mixing the p-xylene crystal slurry in a second stage with a partial flow of final product, heating at about 13° C. and subsequently liberating from the fluid phase still adhering, whereby the p-xylene crystals are drawn off into a heated vessel; drawing off the p-xylene crystals melted in the heated vessel as the final product with the desired purity and also drawing off a partial flow of final product, which is fed back to the second stage of the purifying centrifuge, being heated previously to a temperature of from 60° to 80° C., and feeding the fluid phase separated from the p-xylene crystals to the second stage of the centrifuge for recovery of additional p-xylene which becomes part of the final product stream.

9 Claims, 1 Drawing Sheet

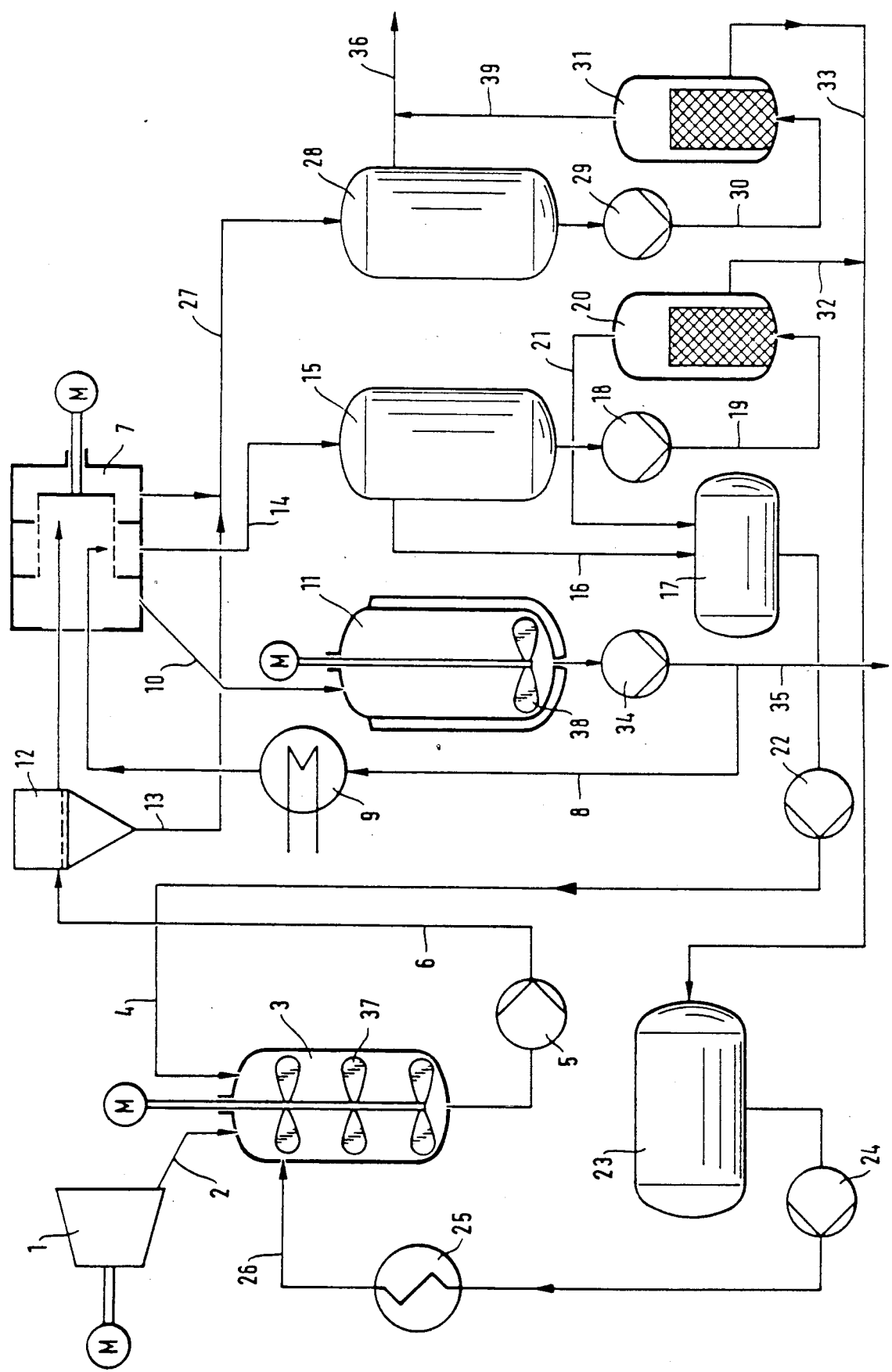

PROCESS FOR MAKING P-XYLENE WITH A PURITY OF MORE THAN 99.8% BY WEIGHT

BACKGROUND OF THE INVENTION

My invention relates to a process for making high purity p-xylene and, more particularly, for making p-xylene with a purity of at least 99.8% by weight from a crude product obtained by crystallization whose purity is about 98% by weight.

Crystallization methods can be used to separate p-Xylene from a $C_8$-aromatic starting material which contains ethyl benzene as well as the three xylene isomers. Use is made of the fact that the melting point of the individual $C_8$ isomers have significant temperature differences. However conventional crystallization methods can be used to make p-Xylene with a purity of greater than 99.5% by weight only with great expense. Thus p-Xylene which was produced in a centrifuge without additional processing with a purity of about 98% by weight is subsequently treated to produce p-Xylene with a purity of over 99.5% by weight in the centrifuge with final products or with suitable media for that which may be separated by distillation from p-Xylene.

Currently p-Xylene with a purity of over 99.8% by weight made by a special adsorption process has been marketed which naturally caused corresponding inquiries about this very pure product.

With the help of crystallization processes up to now however only with great expense and Xylene loss has a p-Xylene product of comparable purity been made so that for the professional engineer a plant operating according to the crystallization process is at a genuine competitive disadvantage.

SUMMARY OF THE INVENTION

It is an object of the present invention to provide an improved process for making p-xylene with at least 99.8% by weight purity from a starting material whose purity is about 98% by weight by crystallization.

Accordingly this object and others are attained in a process of the above-described kind comprising the following process steps:

a) intermixing the crystalline starting material with precooled water and p-Xylene fed back from step e) of this process whose purity is about 96% by weight in a mixer at a temperature of 0° to 13° C., advantageously 5° to 7° C. to form a p-Xylene crystal water mixture;

b) transferring the p-Xylene crystal water mixture produced in the mixer as soon as the crystal composition of the mixture amounts to about 30% by weight continuously into a purifying centrifuge via a dewatering filter by which a crystal composition of up to 70 to 80% by weight results;

c) separating the fluid phase further from the p-Xylene crystals in a first stage of a purifying centrifuge, mixing the precipitating p-Xylene crystal slurry in a second stage with a partial flow of final product, heating at about 13° C. and subsequently liberating from the fluid phase still adhering, whereby the p-Xylene crystals are drawn off into a heated vessel;

d) drawing off the p-Xylene crystals melted in the heated vessel as a final product with the desired purity, also drawing off a partial flow of final product, which is fed back in the second stage of the purifying centrifuge, said partial flow being heated previously to a temperature of from 60° to 80° C., and e) feeding the fluid phase separated from the p-Xylene crystals in the second stage of the purifying centrifuge into a separating vessel, in which the p-Xylene is separated and subsequent to that is fed back into step a) of this process, while the aqueous phase consisting of a water-xylene emulsion and coming down in the separating vessel is broken up into its components in a subsequently connected coalescing unit, which are fed back separately from each other similarly into step a) of the process.

Advantageously in the process between 6 and 20 % by weight of the total precipitating final product is fed back into the second stage of the purifying centrifugation for the purpose of heating the crystal slurry. The heating of the crystal slurry in the second stage of the purifying centrifugation occurs at about 13° C. The heating can be performed by steam, sprayed hot water or hot air.

BRIEF DESCRIPTION OF THE DRAWING

The objects, features and advantages of the present invention will be made more apparent from the following detailed description, reference being made to the accompanying drawing in which:

The sole FIGURE is a flow chart for the process for obtaining p-Xylene which is more than 99.8% by weight.

DETAILED DESCRIPTION OF THE INVENTION

The p-Xylene crystals serving as starting material with a purity of about 98% by weight are fed from the centrifuge 1 and conducted through pipe 2 to a mixer 3 at a temperature of −5° to 7° C. This starting material or preproduct can be obtained according to a crystallization process which is known, since it is known that this process can produce p-Xylene with a purity of about 98% by weight. The p-Xylene crystals originating from the centrifuge 1 have a certain residual moisture, which is about 3 to 6% by weight.

Simultaneously with the p-Xylene crystallization the p-Xylene originating in the vessel 17 whose purity is about 96% by weight is fed over the pipe 4 into the mixer 3. On obtaining this p-Xylene the process goes on in a way described in more detail below. The temperature in the mixer 3 is kept constant between 0° and 13° C., advantageously between 5° and 7° C., by the continuous feeding of water over the pipe 26 with simultaneous discharge of the p-Xylene-crystal-water mixture through the pump 5.

The mixer 3 is provided with a stirrer 37 to keep the partially formed crystal agglomerates in the mixture driven upwardly.

After a dwell time of about 30 seconds the p-xylene-water mixture is fed through the pump 5 over the pipe 6 to the dewatering filter 12. This mixture has a crystal component of about 30% by weight. In dewatering filter 12 so much fluid is drawn off that a concentration of up to a crystal content of from 70 to 80% by weight. The fluid phase is conducted off through pipes 13 and 27 to the separating vessel 28, while the crystal slurry is fed into the purifying centrifuge.

The p-Xylene crystal-water mixture next is dewatered further in a first stage of the purifying centrifuge 7. The fluid phase coming down is drawn off through the pipe 27 into the separating vessel 28, while the resulting p-Xylene crystal slurry is mixed with a partial flow of the final product. This partial flow, which is fed back by the pipe 8 into the second stage of the purifying centrifuge 7 and is heated from 60° to 80° C. in heat exchanger 9 before entry into the purifying centrifuge 7, causes a heating of the predried p-Xylene crystals and a mixing with the fluid phase adhering to the crystals. The p-Xylene crystals subsequently dried and heated in this way to a temperature of about 13° C. leave the purifying centrifuge 7 with a higher purity through the shaft 10 and arrive in the heated vessel 11, which can be provided with a stirrer 38 for improvement of the heat transfer.

The fluid centrifuged off from the p-Xylene crystals is drawn off during this over the pipe 14 into the separating vessel 15. In the heated vessel 11 the p-Xylene crystals are heated up and then pumped as final product with the desired purity of more than 99.8% by weight to the unshown storage container over the pipe 35 by the pump 34. The pipe 8 branches from the pipe 35 and the pipe 8 carries the partial flow of end product which is fed back into the purifying centrifuge 7. The size of this partial flow is from between 6 and 20 by weight of the total end product drawn over the pipe 35.

The fluid collecting in the separating vessel 15 is separated by phase separation into a Xylene phase and an aqueous phase. The xylene phase is drawn off interface-controlled by the pipe 16 to the container 17, while the aqueous phase as the heavy phase is fed through the pump 18 over the pipe 19 into the coalescer 20. Here this phase, which comprises an aqueous-xylene emulsion, is broken up into its components. The xylene is drawn off over the pipe 21 and is united with the xylene located in the container 17, while the water is conducted over the pipe 32 to the pipe 33. The Xylene, whose purity is now about 96% by weight, is fed back through the pipe 4 by the pump 22 into the mixer 3.

The fluid conducted over the pipe 27 into the separating vessel 28 is broken up in it similarly by phase separation into the Xylene phase and an aqueous phase. The Xylene phase is drawn off over the pipe 36. Since its p-Xylene content is about 85 to 87 % by weight, it can be fed back in before the Centrifuge 1 into the crystallization process. The aqueous phase consists of a water-xylene emulsion and is pumped by the pump 29 over the pipe 30 into the coalescer, in which the separation into both components occurs The separated p-Xylene is added to the p-Xylene in the pipe 36 over the pipe 39. The water coming down flows from the coalescer 31 over the pipe 33 into the container 23. From there the water is pumped back by the pump 24 over the pipe 26, since it is cooled in a heat exchanger 25 to a temperature of 2° to 10° C.

Finally the effectiveness of the process according to our invention should be apparent from this embodiment. The p-Xylene serving as a starting material is fed from centrifuge 1 with a purity of 98% by weight and a residual moisture content of about 6% in the mixer 3. The temperature of the p-Xylene is between −2° and 0° C., while precooled water with a temperature of about 9° C. was fed into the mixing container 3. Simultaneously p-Xylene was added over the pipe 4 with a purity of 96.6% by weight and a temperature of 12° C. For each kg of starting material 0.1 kg 96.6% by weight xylene was admixed. The resulting p-xylene crystal-water mixture with a crystal composition of about 30% by weight and a temperature of about 7.5° C. was drawn from the mixer 3 and fed into the dewatering filter 12, in which a concentration of up to a crystal content of 70% by weight was attained. Finally the mixture was fed to the purifying centrifuge 7, in which the further working-up, as described above, occurs. The fused final product drawn off through the pipe 35 has a purity of 99.9% by weight. Of this final product about 10% by weight was drawn off through pipe 8 and after heating to a temperature of 70° C. fed back into the purifying centrifuge 7.

While the invention has been illustrated and described as embodied in a process for obtaining high p-xylene having a purity of greater than 99.8% by weight, it is not intended to be limited to the details shown, since various modifications may be made without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed as new and desired to be protected by Letters Patent is set forth in the appended claims:

1. A process for obtaining a p-xylene final product with a purity of more than 99.8% by weight from a crystalline p-xylene-containing starting material, said starting material being obtained by a crystallization method with a purity of about 98% by weight, comprising the steps of:
    a) intermixing the crystalline p-xylene-containing starting material with precooled water and p-xylene fed back from step e) whose purity is about 96% by weight in a mixer at a temperature of 0° to 13° C. to form a p-xylene-crystal-water mixture containing p-xylene crystals and water;
    b) continuously transferring the p-xylene-crystal-water mixture produced in the mixer as soon as the mixture contains about 30% by weight of said p-xylene crystals into a purifying centrifuge via a dewatering filter, said dewatering filter forming a fluid phase and a p-xylene crystal slurry containing up to 70 to 80% by weight p-xylene crystals;
    c) separating the fluid phase further from the p-xylene crystals in a first stage of said purifying centrifuge, mixing the p-xylene crystal slurry in a second stage with a partial flow of said final product, heating at about 13° C. and subsequently liberating from the fluid phase still adhering, whereby the p-xylene crystals are drawn off into a heated vessel;
    d) drawing off the p-xylene crystals melted in the heated vessel as said final product with said purity and also drawing off said partial flow of said final product, which is fed back to the second stage of the purifying centrifuge, said partial flow being heated previously to a temperature of from 60° to 80° C., and
    e) feeding the fluid phase separated from the p-xylene crystals in the second stage of the purifying centrifuge into a separating vessel to form a p-xylene phase and an aqueous phase consisting of a water-xylene emulsion, separating said p-xylene phase from said water-xylene emulsion and feeding back said p-xylene phase to step a), feeding the aqueous phase into a subsequently connected coalescing unit and breaking up said aqueous phase therein into its components, said components being fed back separately from each other similarly into step a).

2. The process according to claim 1, wherein said temperature in said mixer in step a) is from 5° to 7° C.

3. The process according to claim 1, wherein further comprising feeding back said p-xylene phase from said separating vessel to said method of making said crystalline p-xylene-containing starting material and feeding said water-xylene emulsion to a subsequently connected coalescer and breaking up said water-xylene emulsion in said coalescer into its components and feeding back said components into said method of making said starting material.

4. The process according to claim 1, further comprising feeding back from 6 to 20% by weight of the said final product to the second stage of the purifying centrifuge for heating of the crystal slurry.

5. The process according to claim 4, wherein said heating of said crystal slurry in said second stage of said purifying centrifuge occurs at about 13° C.

6. The process according to claim 5, wherein said heating of said crystal slurry occurs with heated circulating air.

7. The process according to claim 5, wherein said heating of said crystal slurry occurs with steam.

8. The process according to claim 5, wherein said heating of said crystal slurry occurs with sprayed hot water.

9. The process according to claim 1, further comprising maintaining said starting material at a temperature of −5° to 7° C. and feeding the water into the mixer at a temperature of 2° to 10° C.

* * * * *